(12) United States Patent
Shah et al.

(10) Patent No.: US 6,451,346 B1
(45) Date of Patent: *Sep. 17, 2002

(54) BIODEGRADABLE PH/THERMOSENSITIVE HYDROGELS FOR SUSTAINED DELIVERY OF BIOLOGICALLY ACTIVE AGENTS

(75) Inventors: Subodh Shah, Newbury Park; Weiguo Dai, Winnetka, both of CA (US)

(73) Assignee: Amgen Inc, Thousand Oaks, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 days.

(21) Appl. No.: 09/221,178

(22) Filed: Dec. 23, 1998

(51) Int. Cl.$^7$ .......................... A61K 9/10; A61K 47/34
(52) U.S. Cl. .................. 424/486; 514/772.3; 514/944
(58) Field of Search .................. 424/78.08, 486, 424/78.18, 78.26, 426, 428; 514/772.3, 944

(56) References Cited

U.S. PATENT DOCUMENTS

| | | | |
|---|---|---|---|
| 5,410,016 A | * 4/1995 | Hubbell et al. | |
| 5,702,717 A | * 12/1997 | Cha et al. | 424/425 |
| 5,711,958 A | * 1/1998 | Cohn et al. | |
| 5,922,682 A | * 7/1999 | Brich et al. | 514/23 |
| 5,929,196 A | * 7/1999 | Kissel et al. | 528/271 |
| 6,117,949 A | * 9/2000 | Rathi et al. | 525/415 |
| 6,201,072 B1 | * 3/2001 | Rathi et al. | 525/415 |
| 6,211,249 B1 | * 4/2001 | Cohn et al. | |

* cited by examiner

Primary Examiner—Edward J. Webman
(74) Attorney, Agent, or Firm—Craig A. Crandall; Ron K. Levy; Stephen M. Odre

(57) ABSTRACT

The present invention relates generally to the development of pharmaceutical compositions which provide for sustained release of biologically active polypeptides. More specifically, the invention relates to the use of pH/thermosensitive biodegradable hydrogels, consisting of a A-B di block or A-B-A tri block copolymer of poly(d,l- or l-lactic acid) (PLA) or poly(lactide-co-glycolide) (PLGA) (block A) and polyethylene glycol (PEG) (block B), with ionizable functional groups on one or both ends of the polymer chains, for the sustained delivery of biologically active agents.

7 Claims, 4 Drawing Sheets

A: 100% hydroxy-terminated PLGA-PEG-PLGA copolymers
B: 80% hydroxy-terminated + 20% carboxy-terminated PLGA-PEG-PLGA copolymers
C: 50% hydroxy-terminated + 50% carboxy-terminated PLGA-PEG-PLGA copolymers

SEQUENCE LISTING

<160> NUMBER OF SEQ ID NOS: 1

<210> SEQ ID NO 1
<211> LENGTH: 146
<212> TYPE: PRT
<213> ORGANISM: Human Leptin

<400> SEQUENCE: 1

```
Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145
```

BIODEGRADABLE PH/THERMOSENSITIVE HYDROGELS FOR SUSTAINED DELIVERY OF BIOLOGICALLY ACTIVE AGENTS

FIELD OF THE INVENTION

The present invention-relates to the use of biodegradable, pH/thermosensitive hydrogels, consisting of a A-B-A tri block copolymer of poly(d,l- or l-lactic acid) (PLA) or poly(lactide-co-glycolide) (PLGA) (block A) and polyethylene glycol (PEG) (block B), with ionizable functional groups on one or both ends of the polymer chains, for the sustained delivery of biologically active agents.

BACKGROUND OF THE INVENTION

Due to recent advances in genetic and cell engineering technologies, proteins known to exhibit various pharmacological actions in vivo are capable of production in large amounts for pharmaceutical applications. Such proteins include erythropoietin (EPO), novel erythrbpoiesis stimulating protein (NESP), granulocyte colony-stimulating factor (G-CSF), interferons, (alpha, beta, gamma, consensus), tumor necrosis factor binding protein TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), glial cell line derived neurotrophic factor (GDNF) and obesity protein (OB protein). OB protein may also be referred to herein as leptin.

Because proteins such as leptin generally have short in vivo half-lives and negligible oral bioavailability, they are typically administered by frequent injection, thus posing a significant physical burden on the patient (e.g., injection site reactions are particularly problematic with many leptin formulations) and associated administrative costs. As such, there is currently a great deal of interest in developing and evaluating sustained-release formulations. Effective sustained-release formulations can provide a means of controlling blood levels of the active ingredient, and also provide greater efficacy, safety, patient convenience and patient compliance. Unfortunately, the instability of most proteins (e.g. denaturation and loss of bioactivity upon exposure to heat, organic solvents, etc.) has greatly limited the development and evaluation of sustained-release formulations.

Biodegradable polymer matrices have thus been evaluated as sustained-release delivery systems. Attempts to develop sustained-release formulations have included the use of a variety of biodegradable and non-biodegradable polymer (e.g. poly(lactide-co-glycolide)) microparticles containing the active ingredient (see e.g., Wise.et al., *Contraception,* 8:227–234 (1973); and Hutchinson et al., *Biochem. Soc. Trans.,* 13:520–523 (1985)), and a variety of techniques are known by which active agents, e.g. proteins, can be incorporated into polymeric microspheres (see e.g., U.S. Pat. No. 4,675,189 and references cited therein).

Utilization of the inherent biodegradability of these materials to control the release of the active agent and provide a more consistent sustained level of medication provides improvements in the sustained release of active agents. Unfortunately, some of the sustained release devices utilizing microparticles still suffer from such things as: active agent aggregation formation; high initial bursts of active agent with minimal release thereafter; and incomplete release of active agent.

Other drug-loaded polymeric devices have also been investigated for long term, therapeutic treatment of various diseases, again with much attention being directed to polymers derived from alpha hydroxycarboxylic acids, esptcially lactic acid in both its racemic and optically active form, and glycolic acid, and copolymers thereof. These polymers are commercially available and have been utilized in FDA-approved systems, e.g., the Lupron Depot™, which consists of injectable microcapsules which release leuprolide acetate for about 30 days for the treatment of prostate cancer.

Various problems identified with the use of such polymers include: inability of certain macromolecules to diffuse out through the matrix; deterioration and decomposition of the drug (e.g., denaturation caused by the use of organic solvents); irritation to the organism (e.g. side effects due to use of organic solvents); low biodegradability (such as that which occurs with polycondensation of a polymer with a multifunctional alcohol or multifunctional carboxylic acid, i.e., ointments); and slow rates of degradation.

The use of polymers which exhibit reverse thermal gelation have also been reported. For example, Okada et al., Japanese Patent Application 2-78629 (1990) describe biodegradable block copolymers synthesized by transesterification of poly(lactic acid) (PLA) or poly(lactic acid)/glycolic acid (PLA/GA) and poly(ethylene glycol) (PEG). PEGs with molecular weights ranging from 200 to 2000, and PLA/GA with molecular weights ranging from 400 to 5000 were utilized. The resultant product was miscible with water and formed a hydrogel. The Okada et al. reference fails to provide any demonstration of sustained delivery of drugs using the hydrogels.

Cha et al., U.S. Pat. No. 5,702,717 describe systems for parenteral delivery of a drug comprising an injectable biodegradable block copolymeric drug delivery liquid having reverse thermal gelation properties, i.e., ability to form semi-solid gel, emulsions or suspension at certain temperatures. Specifically, these thermosensitive gels exist as a mobile viscous liquidat low temperatures, but form a rigid semisolid gel at higher temperatures. Thus, it is possible to use these polymers to design a formulation which is liquid at room temperature or at lower temperatures, but gels once injected, thus producing a depot of drug at the injection site. The systems described by Cha et al. utilize a hydrophobic A polymer block comprising a member selected from the group consisting of poly(α-hydroxy acids) and poly (ethylene carbonates) and a hydrophilic B polymer block comprising a PEG. The Cha et al. system requires that less than 50% by weight hydrophobic A polymer block be utilized and greater than 50% by weight hydrophilic B polymer block be utilized. Interestingly, however, it appears that several of the disclosed hydrogels might not be commercially useful in that the lower critical solution temperature (LCST) for many of the gels is greater than 37° C. Although Cha et al. propose use of their hydrogels for controlled release of drugs, no such demonstration is provided.

Churchill et al., U.S. Pat. No. 4,526,938, describe a continuous release composition comprising a biodegradable (PLGA/PEG) block copolymer admixed with a drug which is continuously released from the block copolymer. The example described in Churchill et al. uses 50%/50% weight percentage copolymer. Churchill et al. do not discuss whether the compositions exhibit reverse thermal gelation properties, nor teach aqueous solutions of drug-containing block copolymers that are soluble at the time of injection and that undergo gelation as they reach body temperature. Rather, Churchill et al. teach administration of a block copolymer in solid form.

Martini et al., *J. Chem. Soc.,* 90(13):1961–1966 (1994) describe low molecular weight ABA type tri block copolymers which utilize hydrophobic poly(ε-caprolactone) (PCL), and PEG Unfortunately, in vitro degradation rates for these copolymers was very slow, thus calling into question their ability as sustained-release systems.

Stratton et al., PCT/US97/3479 (WO 98/02142) Jan. 22, 1998, describe pharmaceutical compositions comprising a polymeric matrix having thermal gelation properties, for the delivery of proteins. The class of block copolymers described are generically referred to as polyoxyethylene-polyoxypropylene condensates (also known as Pluronics). Unfortunately, only high molecular weight Pluronics at higher concentrations (25–40 wt. %) exhibit thermoreversible gelation, and the very nature of gelation caused by formation of densely packed liquid crystalline phases in concentrated Pluronic solutions limits the applicability of Pluronics in drug delivery.

Kim et al., *J. Appl. Polym. Sci.*, 45:1711 (1992) describe various pH-sensitive hydrogels and the use of such hydrogels to fabricate a glucose-sensitive insulin release device.

Chen and Hoffman, *Nature*, 373:49–52 (1995) described a new generation of 'intelligent' copolymers of thermogelling surfactants and pH-responsive bioadhesive polymers containing ionizable carboxylic groups, that obtain pH and temperature sensitivity. The polymers are prepared by grafting a temperature-sensitive polymer (PNIPAAm) onto a pH-sensitive polymer (PAAc) backbone, and have been shown to possess bioadhesive properties due to the backbone polymer. It is necessary to obtain a graft (or block) copolymer because it was found that random copolymers of the temperature- and pH-sensitive monomers lose their temperature-sensitivity at body temperatures when the levels of the pH-sensitive component are high enough to obtain a sufficiently bioadhesive material. Drawbacks to the copolymers described by Chen and Hoffman are the potentially poor biocompatibility and non-biodegradability of PNIPAAm polymers, and the fact that drugs contained within some NIPAAm-containing hydrogels are known to be effectively squeezed out of the hydrogel as the hydrogel collapses, leading to a burst of drug each time the gel collapses, which is not ideal for sustained drug delivery.

Lee et al., *J. Appl. Polym. Sci.*, 62:301–311 (1996) report on the preparation and swelling properties of pH- and temperature-dependent poly(vinyl alcohol) (PVA)/poly (acrylic acid) (PAAc) interpenetrating polymer networks (IPN) hydrogels by a unique freezing-thawing method. It was reported that the hydrogels showed both positive and negative swelling behaviors depending on PAAc content. It is postulated that the hydrogels could be strong candidates as drug delivery materials, but there is no demonstration of such use.

It is the object of the present invention to provide biodegradable, pH/termosensitive hydrogels for the sustained delivery of drugs. The hydrogels of the present invention utilize copolymer compositions containing ionizable functional groups which provide for instant gelation with trapping of all the biologically active agent within the gel, i.e., no burst, and, importantly, which upon injection, possess improved rates of degradation, de-gelation and clearance of the depot from the injection site, making this class of hydrogels more commercially practical than those previously described.

SUMMARY OF THE INVENTION

In one embodiment, the present invention provides pharmaceutical compositions comprising an effective amount of a biologically active agent incorporated into a polymeric matrix, said polymeric matrix comprising a di block or tri block copolymer which is thermosensitive, exhibits pH-responsive gelation/de-gelation, and is capable of providing for the sustained-release of the biologically active agent.

In another embodiment, the present invention provides a method for the parenteral administration of a biologically active agent in a biodegradable polymeric matrix to a warm blooded animal, wherein a gel depot is formed within the body of said animal and the biologically active agent is released from the depot at a controlled rate concomitant with biodegradation of the polymeric matrix

DETAILED DESCRIPTION OF THE INVENTION

Figure 1:
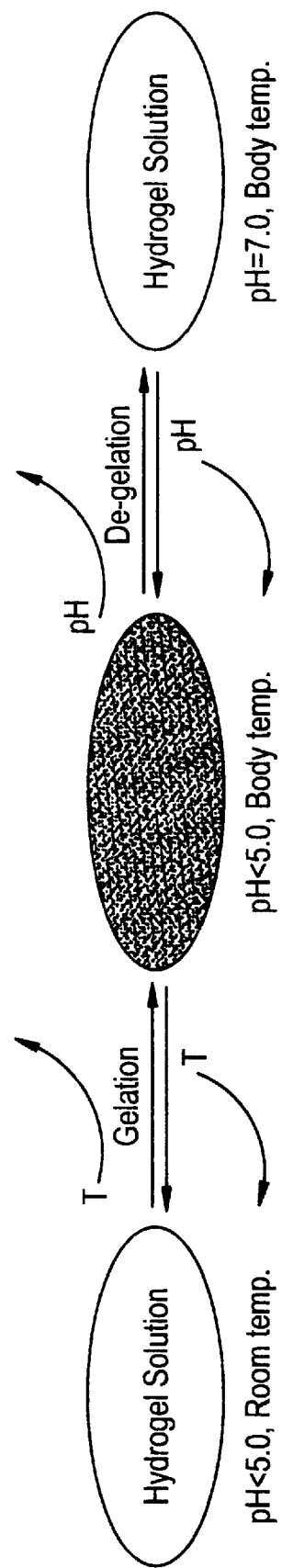
FIG. 1 is a schematic which depicts the pH/thermosensitive nature of the hydrogels of the present invention T=temperature, and the darkened hydrogel depicts the hydrogel in a gelled form, while the clear hydrogel depicts the hydrogel solution form.

As used herein, the following terms shall have the following meaning:

"Reverse thermal gelation temperature" is defined as meaning the temperature below which a copolymer is soluble in water and above which the block copolymer solution forms a semi-solid, i.e. gels, emulsions, dispersions and suspensions.

"LCST", or lower critical solution temperature, is defined as meaning the temperature at which a block copolymer undergoes reverse thermal gelation (solution to gel to solution). For purposes of the present invention, the term "LSCT" can be used interchangeably with "reverse thermal gelation temperature".

"Depot" is defined as meaning a drug delivery liquid which, following injection into a warm blooded animal, has formed a gel upon having the temperature raised to or above the LCST.

"Biodegradable" is defined as meaning that the block copolymer will erode or degrade in vivo to form smaller non-toxic components.

"Parenteral administration" is defined as meaning any route of administration other than the alimentary canal, including, for example, subcutaneous and intramuscular.

For purposes of the present invention, the terms thermosensitive, thermoreversible, and thermoresponsive can be used interchangeably.

The present invention involves utilization of block copolymers having biodegradable hydrophobic ("A") block segments and hydrophilic ("B") block segments. The block copolymers are di block, e.g., A-B, or tri block copolymers, e.g., A-B-A or B-A-B, type block copolymers.

Biodegradable hydrophobic A block segments contemplated for use include poly($\alpha$-hydroxy acid) members derived from or selected from the group consisting of homopolymers and copolymers of poly(lactide)s (d,l- or l-forms), poly(glycolide)s, polyanhydrides, polyesters, polyorthoesters, polyetheresters, polycaprolactone, polyesteramides, polycarbonate, polycyanoacrylate, polyurethanes, polyacrylate, blends and copolymers thereof.

The term "PLGA" as used herein is intended to refer to a polymer of lactic acid alone, a polymer of glycolic acid alone, a mixture of such polymers, a copolymer of glycolic acid and lactic acid, a mixture of such copolymers, or a mixture of such polymers and copolymers. Preferably, the biodegradable A block polymer will be polylactide-co-glycolide (PLGA) The PLGA may be non-ionic, e.g., hydroxy-terminated, or may be ionic, e.g., carboxy-terminated. As relates to the ionic polymers, the ionizable functional groups may be on either one or both ends of the polymer chain, and terminal ionizable groups contemplated for use include any ionizable group having a p$K_a$ 3–8, e.g., carboxylic acids, amines, sulfonic acids, ammonium salts.

The range of molecular weights contemplated for the A block polymers to be used in the present processes can be readily determined by a person skilled in the art based upon such factors the desired polymer degradation rate. Typically, the range of molecular weight for the A block will be 1000 to 20,000 Daltons.

Hydrophilic B block segments contemplated for use include polyethylene glycols having average molecular weights of between about 500 and 10,000. These hydrophilic segments may also contain ionizable groups, if for example, B-A-B type copolymers are used.

The copolymer compositions for the tri block copolymers of the present invention are specially regulated to assure retention of the desired water-solubility and gelling properties, i.e., the ratios must be such that the block copolymers possess water solubility at temperatures below the LCST, and such that there is instant gelation under physiological conditions (i.e. pH 7.0 and 37° C.) so as to minimize the initial burst of drug. In the hydrogels of the present invention the hydrophobic A block makes up 20% to 80% by weight of the copolymer and the hydrophilic B block makes up 80% to 20% of the copolymer.

The concentration at which the block copolymers of the present-invention remain soluble below the LCST is typically up to about 60% by weight, with 10%–30% preferred. The concentration utilized will depend upon the copolymer composition actually used, as well as whether or not a gel or emulsion is desired.

The pH/thermosensitive hydrogels of the present invention comprise ionic block copolymers such that the resultant hydrogels exhibit pH-responsive gelation/de-gelation in addition to the reverse thermal gelation properties (see FIG. 1). The hydrogels may comprise non-ionic block copolymers mixed or "blended" with ionic block copolymers and the weight ratios of ionic block copolymer to non-ionic block copolymer in the blends can be adjusted such that the resultant hydrogels possess the desirable rate of degradation, de-gelation and rate of clearance from the injection site. Because this new class of hydrogels provide for an improved rate of clearance of the hydrogel from the injection site, they are more commercially practicable than those hydrogels and compositions previously described in that they.

The biodegradable, pH/thermosensitive block copolymers of the present invention can be prepared in a two-step procedure which utilizes thermal condensation. In step 1, thermosensitive, hydroxy-terminated A-B-A block copolymers of PLGA/PLA (block A) and PEG (block B) are synthesized by mixing either homopolymer of poly lactide (PLA) or copolymer of poly lactide-co-gycolide (PLGA) with polyethylene glycol (PEG) and allowing di-hydroxy PEG to react with PLGA or PLA at 160° C. under reduced pressure. Different weight ratios of PLGA and PEG were used for thermal condensation to obtain a series of block copolymers with desirable copolymer composition and block lengths. Copolymer composition and relative block lengths were confirmed by $^1$H-NMR spectroscopy. In step 2, the thermosensitive, hydroxy-terminated A-B-A block copolymers are further reacted with, e.g., succinic anhydride, to obtain A-B-A block copolymers with succinic acid groups at one or both ends of the polymer chain, thus providing hydrogels which exhibit thermosensitive/pH-responsive gelation. This two-step procedure is graphically depicted in FIG. 2, Scheme 1.

The biodegradable, ionic block copolymers of the present invention can also be synthesized by single step condensation of PLGA with activated PEG. This procedure is graphically depicted in FIG. 2, Scheme 2.

Alternatively, the thermosensitive, non-ionic block copolymers could be synthesized in a melt process which involves ring opening polymerization of A block using B block as the initiator. In a typical experiment, the A-B-A tri block copolymer is prepared by stannous octoate catalyzed ring-opening polymerization of d,l-dilactide (or PLGA) using $\alpha,\omega$-dihydroxy-terminated PEG as the initiator The mole ratio of B block to d,l-dilactide (or PLGA) is used to control the lengths of the A blocks, and provide a series of polymers with increasing A block contents and hydrophobicities. The relative A and B block lengths can, be confirmed by $^1$H-NMR spectroscopy The process used to mix the copolymers with a biologically active agent and/or other materials involves dissolving the A-B-A tri block copolymers in an aqueous solution, followed by addition of the biologically active agent (in solution, suspension or powder), followed by thorough mixing to assure a homogeneous distribution of the biologically active agent throughout the copolymer Alternatively, the process can involve dissolving the A-B-A tri block copolymer in a biologically active agent-containing solution. In either case, the process is conducted at a temperature lower than the gelation temperature of the copolymer and the material is implanted into the body as a solution which then gels into a depot in the body. In the compositions of the present invention, the biologically active agent will generally have a concentration in the range of 0 to 200 mg/mL.

Buffers contemplated for use in the preparation of the biologically active agent-containing hydrogels are buffers which are all well known by those of ordinary skill in the art and include sodium acetate, Tris, sodium phosphate, MOPS, PIPES, MES and potassium phosphate, in the range of 25 mM to 500 mM and in the pH range of 4.0 to 8.5.

It is also envisioned that other excipients, e.g., various sugars (glucose, sucrose), salts (NaCl, ZnCl) or surfactants, may be included in the biologically active agent-containing hydrogels of the present invention in order to alter the LCST or rate of gelation of the gels. The ability to alter the rate of gelation and/or LCST is important and an otherwise non-useful hydrogel may be made useful by addition of such excipients.

As used herein, biologically active agents refers to recombinant or naturally occurring proteins, whether human or animal, useful for prophylactic, therapeutic or diagnostic application. The biologically active agent can be natural, synthetic, semi-synthetic or derivatives thereof. In addition, biologically active agents of the present invention can be perceptible. A wide range of biologically active agents are contemplated. These include but are not limited to hormones, cytokines, hematopoietic factors, growth factors, antiobesity factors, trophic factors, anti-inflammatory factors, small molecules and enzymes (see also U.S. Pat. No 4,695,463 for additional examples of useful biologically active agents). One skilled in the art will readily be able to adapt a desired biologically active agent to the compositions of present invention.

Proteins contemplated for use would include but are not limited to interferon consensus (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), stem cell factor (PCT Publication Nos. 91/05795, 92/17505 and 95/17206, hereby incorporated by reference including drawings), and leptin (OB protein) (see PCT publication Nos. 96/40912, 96/05309, 97/00128, 97/01010 and 97/06816 hereby incorporated by reference including figures).

Figure 3:
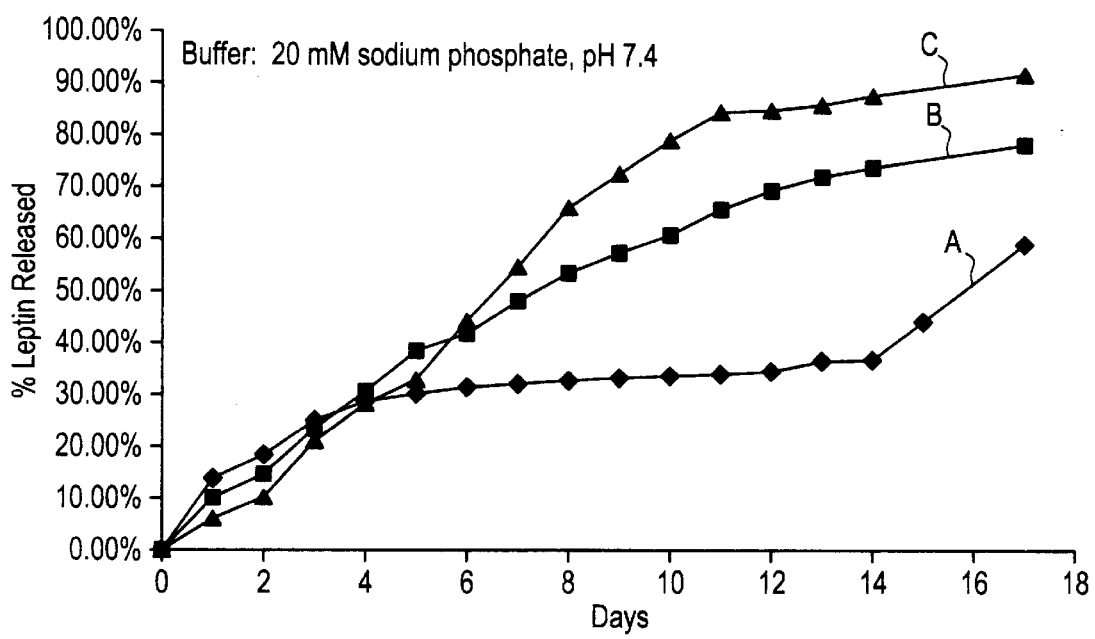
FIG. 3 depicts the in vitro release characteristics of leptin released from various hydrogels. The -♦- depicts the release from a 100% hydroxy-terminated PLGA-PEG-PLGA hydrogel; —■- depicts the release from a 80% hydroxy-terminated+20% carboxy-terminated PLGA-PEG-PLGA hydrogel (weight ratio); and -▲- depicts the release from a 50% hydroxy-terminated+50% carboxy-terminated PLGA-PEG-PLGA hydrogel (weight ratio). % protein released is plotted vs. time (days).
Figure 4:
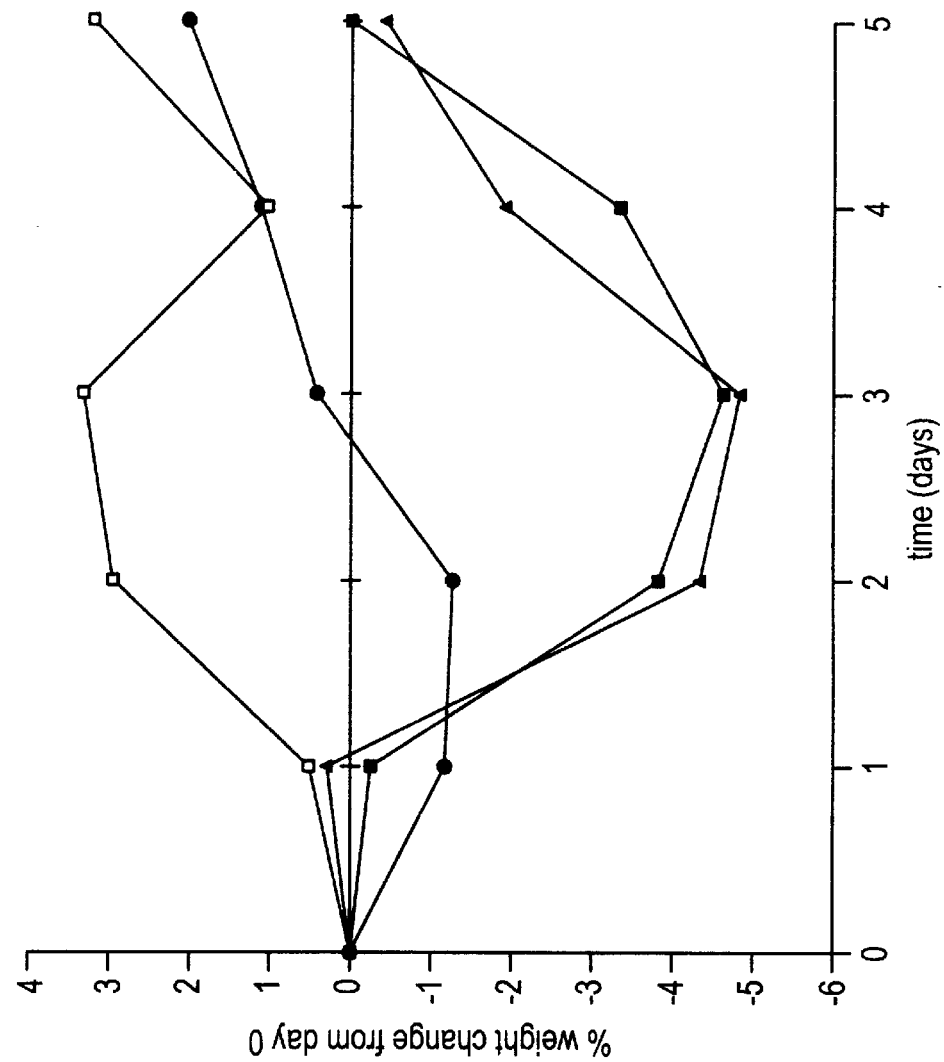
FIG. 4 depicts the in vivo bioactivity of various leptin-containing hydrogel formulations. The - — represents the buffer control (0.1 ml of 10 mM acetate buffer, pH 4.0, (day 0 only)); -●- represents the leptin control (0.1 ml of 20 mg/ml (100 mg/kg) leptin formulated in 10 mM acetate buffer, pH 4.0 (day 0 only)); -▲- represents 0.1 ml of a 95% hydroxy-terminated+5% carboxy-terminated PLGA-PEG-PLGA hydrogel (weight ratio) consisting of 20 mg/ml (100 mg/kg) leptin, in 10 mM acetate, pH 4.0 (day 0 only); and —■- represents 0.1 ml of a 70% hydroxy-terminated +30% carboxy-terminated PLGA-PEG-PLGA hydrogel (weight ratio) consisting of 20 mg/ml (100mg/kg) leptin, in 10 mM acetate, pH 4.0 (day 0 only). % body weight change (from the day 0 body weight) is plotted vs. time (days).

The type of leptin used for the present preparations may be selected from those described in PCT International Publication Number WO 96/05309, as cited above and herein incorporated by reference in its entirety. FIG. 3 of that publication (as cited therein SEQ ID NO: 4) depicts the full deduced amino acid sequence derived for human leptin (referred to as the human "OB" protein). The amino acids are numbered from 1 to 167. A signal sequence cleavage site is located after amino acid 21 (Ala) so that the mature protein extends from amino acid 22 (Val) to amino acid 167 (Cys). For the present disclosure, a different numbering is used herein, where the amino acid position 1 is the valine residue which is at the beginning of the mature protein. The amino acid sequence for mature, recombinant methionyl human leptin is presented herein as SEQ ID NO: 1, where the first amino acid of the mature protein is valine (at position 1) and a methionyl residue is located at position −1 (not included in the sequence below).
SEQ ID NO: 1
V P I Q K V Q D D T K T L I K T I V T R I N D I S H
T Q S V S S K Q K V T G L D F I P G L H P I L T L S K
M D Q T L A V Y Q Q I L T S M P S R N V I Q I S N D
L E N L R D L L H V L A F S K S C H L P W A S G L E
T L D S L G G V L E A S G Y S T E V V A L S R L Q G
S L Q D M L W Q L D L S P G C
However, as with any of the present leptin moieties, the methionyl residue at position −1 may be absent.

Alternatively, one may use a natural variant of human leptin, which has 145 amino acids and, as compared to rmetHu-leptin of SEQ ID NO: 1, has a glutamine absent at position 28.

Generally, the leptin moiety for human pharmaceutical use herein will be capable of therapeutic use in humans (see also, animal leptins, below). Thus, one may empirically test activity to determine which leptin moieties may be used. As set forth in WO96/05309, leptin protein in its native form, or fragments (such as enzyme cleavage products) or other truncated forms and analogs may all retain biological activity. Any of such forms may be used as a leptin moiety for the present preparations, although such altered forms should be tested to determine desired characteristics. See also, PCT International Publication Numbers WO 96/40912, WO 97/06816, 97/18833, WO 97/38014, WO 98/08512and WO 98/28427, herein incorporated by reference in their entireties.

One may prepare an analog of recombinant human leptin by altering amino acid residues in the recombinant human sequence, such as substituting the amino acids which diverge from the murine sequence. Murine leptin is substantially homologous to human leptin, particularly as a mature protein and, further, particularly at the N-terminus. Because the recombinant human protein has biological activity in mice, such an analog would likely be active in humans. For example, in the amino acid sequence of native human leptin as presented in SEQ ID NO: 1, one may substitute with another amino acid one or more of the amino acids at positions 32, 35, 50, 64, 68, 71, 74, 77, 89, 97, 100, 101, 105, 106, 107, 108, 111, 118, 136, 138, 142 and 145. One may select the amino acid at the corresponding position of the murine protein (see Zhang et al., 1994, supra) or another amino acid.

One may further prepare "consensus" molecules based on the rat OB protein sequence. Murakami et al., *Biochem. Biophys. Res. Comm.*, 209:944–52 (1995) herein incorporated by reference. Rat OB protein differs from human OB protein at the following positions (using the numbering of SEQ ID NO: 1): 4, 32, 33, 35, 50, 68, 71, 74, 77, 78, 89, 97, 100, 101, 102, 105, 106, 107, 108, 111, 118, 136, 138 and 145. One may substitute with another amino acid one or more of the amino acids at these divergent positions. The positions underlined are those in which the murine OB protein as well as the rat OB protein are divergent from the human OB protein and, thus, are particularly suitable for alteration. At one or more of the positions, one may substitute an amino acid from the corresponding rat OB protein, or another amino acid.

The positions from both rat and murine OB protein which diverge from the mature human OB protein are 4, 32, 33, 35, 50, 64, 68, 71, 74, 77, 78, 89, 97, 100, 101, 102, 105, 106, 107, 108, 111, 118, 136, 138, 142 and 145. An OB protein according to SEQ ID NO: 1 having one or more of the above amino acids replaced with another amino acid, such as the amino acid found in the corresponding rat or murine sequence, may also be effective.

In addition, the amino acids found in rhesus monkey OB protein which diverge from the mature human OB protein are (with identities noted in parentheses in one letter amino acid abbreviation): 8 (S), 35 (R), 48 (V), 53 (Q), 60 (I), 66 (I), 67 (N), 68 (L), 89 (L), 100 (L), 108 (E), 112 (D) and 118 (L). Since the recombinant human OB protein is active in cynomolgus monkeys, a human OB protein according to SEQ ID NO: 1 having one or more of the rhesus monkey divergent amino acids replaced with another amino acid, such as the amino acids in parentheses, may be effective. It should be noted that certain rhesus divergent amino acids are also those found in the above murine and rat species (positions 35, 68, 89, 100, 108 and 118). Thus, one may prepare a murine/rat/rhesus/human consensus molecule (using the numbering of SEQ ID NO: 1) having one or more of the amino acids replaced by another amino acid at positions: 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142 and 145. The positions underlined are those in which all three species are divergent from human OB protein. A particularly preferred human leptin analog is one wherein the amino acids at position 100 (Trp) or 138 (Trp), and more preferably, both positions are substituted with another amino acid, preferably Gln.

Other analogs may be prepared by deleting a part of the protein amino acid sequence. For example, the mature protein lacks a leader sequence (−22 to −1). One may prepare the following truncated forms of human OB protein molecules (using the numbering of SEQ ID NO 1):

(i) amino acids 98–146;

(ii) amino acids 1–99 and (connected to) 112–146;

(iii) amino acids 1–99 and (connected to) 112–146 having one or more of amino acids 100–111 sequentially placed between amino acids 99 and 112.

In addition, the truncated forms may also have altered one or more of the amino acids which are divergent (in the murine, rat or rhesus OB protein) from human OB protein. Furthermore, any alterations may be in the form of altered amino acids, such as peptidomimetics or D-amino acids.

It is desirable to have such protein containing sustained-release compositions as such compositions could serve to enhance the effectiveness of either exogenously administered or endogenous protein, or could be used, for example, to reduce or eliminate the need for exogenous protein administration.

Moreover, because the materials utilized in the present invention are biocompatible and biodegradable, use of the protein compositions of the present invention help prevent adverse injection site reactions sometimes associated with injections of various proteins such as leptin.

In addition, biologically active agents can also include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), tumor necrosis factor (TNF), tumor necrosis factor-binding protein (TNF-bp), interleukin-1 receptor antagonist (IL-1ra), brain derived neurotrophic factor (BDNF), glial derived neurotrophic factor (GDNF), neurotrophic factor 3 (NT3), fibroblast growth factors (FGF), neurotrophic growth factor (NGF), insulin-like growth factors (IGFs), macrophage colony stimulating factor (M-CSF), granulocyte macrophage colony stimulating factor (GM-CSF), megakaryocyte derived growth factor (MGDF), novel erythropoiesis stimulating protein, keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof.

Also included are those polyptides with amino acid substitutions which are "conservative" according to acidity, charge, hydrophobicity, polarity, size or any other characteristic known to those skilled in the art. See generally, Creighton, Proteins, W. H. Freeman and Company, N.Y., (1984) 498 pp. plus index, passim. One may make changes in selected amino acids so long as such changes preserve the overall folding or activity of the protein. Small amino terminal extensions, such as an amino-terminal methionine residue, a small linker peptide of up to about 20–25 residues, or a small extension that facilitates purification, such as a poly-histidine tract, an antigenic epitope or a binding domain, may also be present. See, in general, Ford et al., *Protein Expression and Purification* 2:95–107 (1991), which is herein incorporated by reference. Polypeptides or analogs thereof may also contain one or more amino acid analogs, such as peptidomimetics.

In general, comprehended by the invention are pharmaceutical compositions comprising effective amounts of chemically modified protein, or derivative products, together with pharmaceutically acceptable diluents, preservatives, solubilizers, emulsifiers, adjuvants and/or carriers needed for administration. (See PCT 97/01331 hereby incorporated by reference.) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs 1435–1712 (1990)).

The pharmaceutical compositions of the present invention are administered as a liquid via intramuscular or subcutaneous route and undergo a phase change wherein a gel is formed within the body, since the body temperature will be above the gelation temperature of the material. The release rates and duration for the particular biologically active agents will be a function of, inter alia, hydrogel density and the molecular weight of the agent.

Therapeutic uses of the compositions of the present invention depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like interferons (see, U.S. Pat. Nos. 5,372,808, 5,541,293, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,999,291, 5,581,476, 5,582,823, 4,810, 643 and PCT Publication No. 94/17185, hereby incorporated by reference including drawings), stem cell factor (PCT Publication Nos. 91/05795, 92/17505 and 95/17206, hereby incorporated by reference including drawings), novel erythropoiesis stimulating protein (PCT Publication No. 94/09257, hereby incorporated by reference including drawings), and the OB protein (see PCT publication Nos. 96/40912, 96/05309, 97/00128, 97/01010 and 97/06816 hereby incorporated by reference including figures). In addition, the present compositions may also be used for manufacture of one or more medicaments for treatment or amelioration of the conditions the biologically active agent is intended to treat.

In the sustained-release compositions of the present invention, an effective, amount of active ingredient will be utilized. As used herein, sustained release refers to the gradual release of active ingredient from the polymer matrix, over an extended period of time. The sustained release can be continuous or discontinuous, linear or non linear, and this can be accomplished using one or more polymer compositions, drug loadings, selection of excipients, or other modifications. The sustained release will result in biologically effective serum levels of the active agent (typically above endogenous levels) for a period of time longer than that observed with direct administration of the active agent. Typically, a sustained release of the active agent will be for a period off days to weeks, depending upon the desired therapeutic effect.

The following examples are offered to more fully illustrate the invention, but are not to be construed as limiting the scope thereof.

Materials

Low molecular weight (Mn 2000–6000) PLGA (poly lactic acid-co-glycolic acid) and PLA (poly lactic acid) were synthesized by direct thermal condensation of glycolic acid and lactic acid at 180° C. under reduced pressure High molecular weight PLGAs were obtained from B.I. Chemicals. Polyethylene glycols (PEG) were obtained from Fluka Chemicals. Leptin, zinc-leptin, G-CSF, Fc-Leptin, and Fc-OPG were obtained from Amgen Inc. All other chemicals are from sources well known in the art.

EXAMPLE 1

Figure 2:
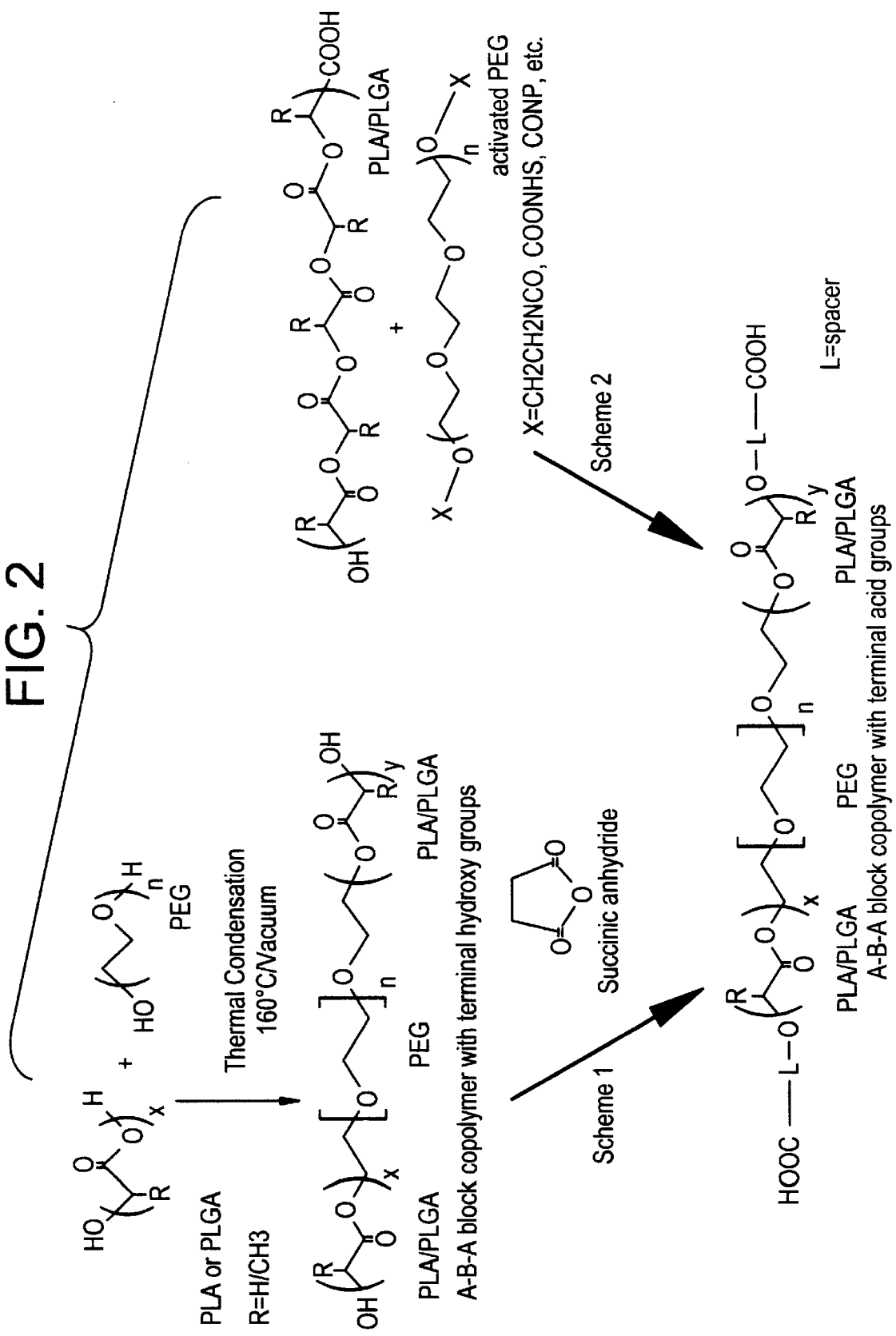
FIG. 2 depicts the two methods by which the A-B-A tri block copolymers of the present invention can be prepared.

This example describes synthesis of a hydroxy-terminated A-B-A (PLGA-PEG-PLGA), tri block copolymer by thermal condensation (FIG. 2, Scheme 1a).

30 grams PLGA (75%/25% LA/GA ratio) (Mn 3740, MW 7050) and 10.7 grams polyethylene glycol (MW 1000) were placed into a three-neck round bottom flask equipped with a thermometer, a nitrogen gas inlet, and a distillation condenser connected to a vacuum pump. After addition of the polymers, the temperature of the reaction mixture was raised slowly to 160° C. under nitrogen purging. The condensation reaction was further carried out at 160° C. for 14 hours under 500 millitorr pressure and with continuous bubbling of dry nitrogen gas. At the end of the condensation reaction, the reaction mixture was cooled, dissolved in methylene chloride and precipitated with an excess of cold isopropanol.

The isolated polymer was dried at 40° C. under vacuum for 48 hours. The molecular weight of the block copolymer was determined by gel permeation chromatography (GPC) using polystyrene standards. The copolymer composition and relative block lengths were determined by $^1$H-NMR.

The PLGA-PEG-PLGA tri block copolymer dissolved either in 100 mM sodium acetate, pH 6.0, or 100 mM sodium phosphate, pH 7.0, exhibited a unique thermoreversible property (solution below room temperature and gel above room temperature, sol-gel-sol) with lower critical solution temperature (LCST) at about 30° C. to 35° C.

EXAMPLE 2

This example describes modification of hydroxy-terminated PLGA-PEG-PLGA tri block copolymer to carboxylic acid-terminated PLGA-PEG-PLGA tri -block copolymer (FIG. 2, Scheme 1b).

To a hydroxy-terminated PLGA-PEG-PLGA copolymer (30grams) described in Example 1, 120 ml of anhydrous 1,4-dioxane was added under continuous nitrogen purging. After complete dissolution of the polymer, 8.57 grams of succinic anhydride (Sigma) in 1,4-dioxane was added, followed by addition of 1.9 grams triethylamine (Aldrich) and 2.3 grams of 4-dimethylaminopyridine (Aldrich). The reaction mixture was stirred at room temperature for 24 hours under nitrogen atmosphere. The conversion of terminal hydroxyl groups to carboxylic acid groups was followed by IR spectroscopy. After completion of the reaction the crude block polymer was isolated by precipitation using ether. The crude acid-terminated polymer was further purified by dissolving the polymer in methhylene chloride (40 ml)land precipitating from ether. The isolated polymer was dried at 40° C. under vacuum for 48 hours. The dried acid-terminated block copolymer (21 grams) was dissolved in400 ml of 100 mM sodium phosphate buffer (pH 7.4), and filtered through 0.45 $\mu$m filter. The polymer solution was then placed in a dialysis membrane (2,000 Molecular Weight cut-off) (Spectrum) and dialyzed against deionized water at 4° C. After dialysis, the polymer solution was lyophilized and the dried polymer was stored at −20° C. under a nitrogen environment.

The molecular weight of the tri block copolymer was determined by gel permeation chromatography (GPC) using polystyrene standards. The copolymer composition and relative block lengths were determined by $^1$H-NMR.

The carboxy-terminated PLGA-PEG-PLGA tri block copolymer dissolved in 100 mM sodium acetate, pH 4.8 exhibited similar thermoreversible gelation as described in Example 1 (solution below room temperature and gel above room temperature, sol-gel-sol) with lower critical solution temperature (LCST) of about 30° C. to 35° C. The carboxy-terminated PLGA-PEG-PLGA tri block hydrogel also demonstrated complete de-gelation as the pH of the hydrogel gradually increased from acidic to neutral under physiological conditions.

EXAMPLE 3

This example describes synthesis of carboxylic acid-terminated PLGA-PEG-PLGA tri block copolymers using different weight ratios of PLGA to PEG.

The synthesis procedures described in Examples 1 and 2 were utilized to prepare carboxy-terminated PLGA-PEG-PLGA tri block copolymers with various PLGA to PEG ratios (See Table 1 below). All the tri block copolymers listed below showed thermoreversible gelation (sol-gel-sol), with LCST in the range of 25° C.–35° C.

TABLE 1

| Polymer | PEG (MW) | PLGA (MW) (Mn) | PLGA (LA/GA molar ratio) | PLGA/PEG (w/w) |
|---|---|---|---|---|
| 1 | 1000 | 3550 | 75/25 | 64/36 |
| 2 | 1000 | 3550 | 75/25 | 66/34 |
| 3 | 1000 | 3550 | 75/25 | 70/30 |
| 4 | 1000 | 4200 | 75/25 | 72/28 |
| 5 | 1000 | 3500 | 75/25 | 74/26 |
| 6 | 1000 | 3500 | 75/25 | 76/24 |
| 7 | 1000 | 3158 | 100/0 | 72/28 |
| 8 | 1000 | 3557 | 56/44 | 72/28 |

EXAMPLE 4

This example describes synthesis of carboxylic acid-terminated PLGA-PEG-PLGA tri block copolymer by condensation of PLGA with activated PEG. (FIG. 1, Scheme 2).

Under a nitrogen stream, 1 gram PEG-bis-isocynate (NCO-PEG-NCO, MW 980from Shearwater Polymers, Inc.), 2.3 grams PLGA (Mn 1652, polydispersity 1.4) and 1.1 grams dibutyltin dilaurate (Aldrich) were added to a 100 ml flask with 30 ml anhydrous methylene chloride. The reaction mixture was stirred at room temperature for 24 hours under nitrogen environment. The reaction was followed by IR spectrophotometer. After completion of the reaction a crude polymer was isolated from the solution by precipitation using excess of diethyl ether/petroleum ether (50/50 (v/v)). The isolated polymer was dried at 40° C. under vacuum for 48 hours. The dried acid terminated block copolymer (2 grams) was dissolved in 38 ml of 100 mM sodium phosphate buffer (pH 7.4), and filtered through a 0.45 µm filter. The polymer solution was placed in a dialysis membrane (2,000 Molecular Weight cut-off) (Spectrum) and dialyzed against deionized water at 4° C. After dialysis, the polymer solution was lyophilized and the dried polymer was stored at −20° C. under nitrogen environment.

The molecular weight of the tri block copolymer was determined by gel permeation chromatography (GPC) using polystyrene standards. The copolymer composition and relative block lengths were determined by $^1$H-NMR. The tri block copolymer synthesized by this method exhibited similar pH/thermoreversiible gelation as described in above examples.

EXAMPLE 5

The following example demonstrates pH dependent gelation of the carboxy-terminated PLGA-PEG-PLGA tri block copolymer solution.

The carboxy-terminated PLGA-PEG-PLGA tri block copolymer described in Example 2 was dissolved in 50 mM sodium acetate or sodium phosphate buffers to obtain 30% (by weight) polymer solution with final pH in the range of 4.0–8.0 One milliliter polymer solution, formulated in different pH buffers, was placed in a glass vial at 37° C. and the gelation was monitored visually as a function of time. The results are summarized in Table 2. As depicted in Table 2, the carboxy-terminated tri block copolymer solution showed pH dependent gelation with no sol-gel property at any time above pH 6.5. All the tri block copolymers listed in Table 1 (Example 3) showed similar pH sensitive gelation at 37° C.

TABLE 2

| Initial hydrogel pH | Gel formation at 37° C. |
| --- | --- |
| 4 | quick gel |
| 4.5 | quick gel |
| 5.0 | quick gel |
| 5.5 | quick gel |
| 6.0 | slow gelation |
| 6.5 | highly viscous solution |
| 7.0 | no gel any time |
| 7.4 | no gel any time |
| 8.0 | no gel any time |

EXAMPLE 6

The following example demonstrates pH dependent de-gelation (gel to solution) of the carboxy-terminated PLGA-PEG-PLGA hydrogel.

The carboxy-terminated PLGA-PEG-PLGA tri block-copolymer described in Example 2 was dissolved in 50 mM sodium acetate buffer to obtain 30% (by weight) polymer solution with final pH 4.5. One milliliter polymer solution was placed into dialysis cassettes (MW cutoff 10,000) (Pierce). The cassettes were then placed in a 37° C. incubator to ensure gelation of the hydrogel inside the dialysis cassettes. Upon complete gelation, each cassette was placed in a beaker containing 500 ml buffer with various pHs ranging from 4.0 to 7.4 and incubated at 37° C. The consistency of the gel at different pHs was monitored as a function of time over one week period. The observations are summarized in Table 3. As depicted in Table3, the hydrogel from the cassette degelled into a solution, due to increase in a pH of the hydrogel during buffer exchange with external buffer when the pH of the external medium was 6.5 or higher. The gel remains intact and firm at all pHs below 6.0. The experiment suggests that the invented acid-terminated PLGA-PEG-PLGA tri block copolymer hydrogel is pH-responsive to a change in surrounding pH. All the block copolymers listed in Table 1 (Example 3) showed similar degelation at closer to neutral pH

TABLE 3

| External Buffer | Hydrogel morphology |
| --- | --- |
| pH 4.0 | gel over one week |
| pH 5.0 | gel over one week |
| pH 5.5 | gel over one week |
| pH 6.0 | soft gel in 2–3 days and solution within one week |
| pH 7.4 | solution in 1–2 hours |

EXAMPLE 7

This example demonstrates manipulation of the rate of de-gelation of the hydrogel by blending carboxy-terminated PLGA/PEG block copolymers with hydroxy-terminated PLGA/PEG block copolymers.

30% (by weight) solutions of hydroxy-terminated PLGA-PEG-PLGA tri block copolymer described in Example 1 (Polymer A) and carboxylic acid-terminated PLGA-PEG-PLGA tri block copolymer described in Example 2 (Polymer B) were prepared separately by dissolving the polymers in 50 mM sodium acetate buffer. The final pHs of both the solutions were adjusted to 4.5 using dilute solutions of either hydrochloric acid or sodium hydroxide. The two polymer solutions were mixed together with different proportions to obtain solutions of polymer blends with various weight ratios of polymer A to polymer B.

One ml of each polymer blend solutions was placed in an individual dialysis cassette (MW cutoff 10,000) (Pierce), and the cassettes were then placed in a 37° C. incubator to ensure gelation of the hydrogel inside the dialysis cassettes. Upon complete gelation the cassettes were placed in a beaker containing 500 ml sodium phosphate buffer, pH 7.4, incubated at 37° C. The consistency of the hydrogel and rate of de-gelation (conversion of the hydrogel into a solution) was monitored as a function of time over one week period. The observations are summarized in Table 4. As depicted in Table 4 the rate of de-gelation of the hydrogel, under physiological conditions, was increased with increasing the amount of carboxylic acid terminated block copolymer in the blend.

TABLE 4

| Sample (by weight %) | Degelation rate |
| --- | --- |
| 100% A | Firm gel over one week |
| 80% A + 20% B | Soft gel after 4 days Viscous solution after 1 week |
| 50% A + 50% B | Solution within 6–10 hours |
| 100% B | Solution within 1 hour |

A: Hydroxy-terminated PLGA-PEG-PLGA copolymers
B: Carboxy-terminated PLGA-PEG-PLGA copolymers

EXAMPLE 8

This example demonstrates clearance of the hydrogel depot from the injection site of normal mice.

The hydrogel solutions with different weight ratios of hydroxy-terminated and carboxy-terminated PLGA-PEG-PLGA tri block copolymers were prepared as described in example 7. Mice were injected subcutaneously with 100 μl of the hydrogel blend solutions. At desirable time points 2 mice from each group were sacrificed by carbon dioxide asphyxiation. A small incision was made near the site of injection and the skin was peeled back carefully so as not to disturb the hydrogel depot. After exposing the injection site, surrounding tissues were carefully dissected away to allow clear observation of the surrounding tissue and the hydrogel depot. The gross visual observation was recorded and the injection sites were photographed using polaroid camera. The observations are summarized in Table 5. As depicted in Table 5, the rate of disappearance of the hydrogel depot from the injection site was gradually increased with increasing the amount carboxy-terminated tri block copolymer in the hydrogel blend.

TABLE 5

| Sample (by weight %) | Clearance from injection site |
| --- | --- |
| 100% A | 4–6 weeks |
| 90% A + 10% B | 2–3 weeks |
| 80% A + 20% B | 3 days |
| 70% A + 30% B | 1 day |
| 100% B | 1–2 hours |

A: Hydroxy-terminated PLGA-PEG-PLGA copolymers
B: Carboxy-terminated PLGA-PEG-PLGA copolymers

EXAMPLE 9

This example describes the preparation of a leptin/hydrogel formulation and the methods used to determine the in vitro release kinetics, and in vivo bioactivity of the leptin/hydrogel formulation.

Preparation of Leptin/Hydrogel Formulation

The hydroxy-terminated PLGA-PEG-PLGA tri block copolymer described in Example 1 and carboxy-terminated PLGA-PEG-PLGA block copolymer described in Example 2 were dissolved separately in 50 mM sodium acetate buffer, pH 6.0. The two polymer solutions were mixed with different proportions to obtain blends with various ratios f carboxy-terminated to hydroxy-terminated copolymers. Leptin solution (formulated in 10 mM acetate, pH 4.0) was slowly added to the hydrogel solution and the mixture was gently swirled on an orbital shaker at 50° C. to assure a homogeneous mixing of leptin throughout the hydrogel solution. The final concentration of the copolymer was 28% (by weight) with pH4.5. The leptin concentration in leptin/hydrogel formulations was 20 mg/ml. The final leptin/hydrogel formulation was filtered through 0.2 μm filter and stored either as a solution at 5° C. or stored as a frozen mass at −20° C.

In Vitro Release Study

The in vitro release of leptin from the leptin/hydrogel formulation was carried out in 20 mM sodium phosphate, pH 7.4, at 37° C. One gram of leptin/hydrogel solution formulation was placed in a glass vial at 37° C. Upon gelation of the leptin/hydrogel formulation, 1 ml of 20 mM phosphate, pH 7.4, buffer was added directly above and in contact with, the gel. The amount of leptin released in the top buffer phase was determined by UV spectrophotometer at 280 nm as well as by SEC-HPLC at 220 nm. To maintain a perfect sink condition the aqueous receptor phase above the gel was completely removed at definite time intervals and replaced by fresh buffer The % leptin released over time is depicted in FIG. 2. The integrity of the leptin released from the hydrogel formulation was confirmed by gel & HPLC.

In Viva Bioactivity

The in vivo bioactivity of leptin/hydrogel formulations were evaluated in normal mice.

Mice were injected subcutaneously (s.c.) with either: a) 0.1 ml of 10 mM acetate buffer, pH 4.0, (n=5, day 0 only); (b) 0.1 ml of 20 mg/ml leptin formulated in 10 mM acetate buffer, pH 4.0 (n=5, 100 mg/kg, day 0 only); (c) 0.1 ml of a leptin/hydrogel blend solution (95% hydroxy-terminated+ 5% carboxy-terminated polymer) (w/w)) formulation consisting of 20 mg/ml leptin, in 10 mM acetate, pH 4.0 (n=5, 100 mg/kg, day 0 only); (d) 0.1 ml of a leptin/hydrogel blend solution (70% hydroxy-terminated+30% carboxy-terminated polymer) (w/w)) formulation consisting of 20 mg/ml leptin, in 10 nM acetate, pH 4.0 (n=5, 100 mg/kg , day 0 only).

% body weight change (from the day 0 body weight) was determined by weighing the animals daily until the body weight of the animals injected with sample (b), (c) and (d) reached the body weights of the animals injected with buffer control (sample (a)). Importantly, a single s.c. injection of 100 mg/kg leptin/hydrogel formulations (samples (c), (d)) showed sustained weight loss in normal mice over a 5 day period (FIG. 3).

EXAMPLE 10

This example describes the incorporation of Fc-leptin into the hydrogel and the results of in vitro release studies using the formulation.

Fc-leptin solution (formulated in 10 mM phosphate, 2.7% arginine, 0.01% Tween-20, pH 6.0) was added to the copolymer hydrogel blend solution (formulated in 50 mM acetate, pH 6.0) as described in Example 7. The final concentration of the copolymer in the Fc-leptin/hydrogel formulation was 10–30% (w/w) and the Fc-leptin concentration was in the range of 20 mg/ml. The in vitro release of Fc-leptin from the hydrogel was carried out in 20 mM sodium phosphate buffer, pH 7.4, at 37° C. as described in Example 9. The Fc-leptin/hydrogel formulation showed sustained release of Fc-leptin over a 7–10 day period of time.

EXAMPLE 11

This example describes the incorporation of BDNF into the hydrogel and the results of in vitro release studies using the formulation.

BDNF solution (formulated in 10 mM sodium phosphate, 150 mM sodium chloride, pH 7.0) was added to the copolymer hydrogel blend solution (formulated in 50 mM acetate, pH 6.0) as described in Example 7. The final concentration of the copolymer in the BDNF/hydrogel formulation was 20–30% (w/w) and the BDNF concentration was in the range of 20 mg/ml. The in vitro release of BDNF from the hydrogel was carried out in 20 mM sodium phosphate buffer, pH 7.4, at 37° C. as described in Example 9. The release of BDNF could be maintained over a 6–9 day period of time.

The present invention has been described in terms of particular embodiments found or proposed to comprise preferred modes for the practice of the invention. It will be appreciated by those of ordinary skill in the art that, in light of the present disclosure, numerous modifications and changes can be made in the particular embodiments exemplified without departing from the intended scope of the invention.

What is claimed is:

1. A pharmaceutical composition for the sustained administration of an effective amount of a protein, comprising an injectable biodegradable polymeric matrix into which said protein has been incorporated, said polymeric matrix having reverse thermal gelation properties and pH-responsive gelation/de-gelation properties; wherein said polymeric matrix is a biodegradable block copolymer comprising:
   (a) 55% to 80% by weight of a hydrophobic A polymer block comprising poly lactide-co-glycolide (PLGA) having an average molecular weight of between 1000–20,000; and
   (b) 20% to 45% by weight of a hydrophilic B polymer block comprising a polyethylene glycol having an average molecular weight of between 500–10,000; and wherein said biodegradable block copolymer has ionizable functional groups on one or both ends of the polymer chains.

2. The composition of claim 1, wherein said ionizable functional groups have a $pK_a$ in the range of 3–8.

3. The composition of claim 2, wherein said hydrophobic A polymer block is poly lactide-co-glycolide (PLGA).

4. The composition of claim 3, wherein said block copolymer is a tri block copolymer having a configuration selected from the group consisting of A-B-A and B-A-B block segments.

5. The composition of claim 4, wherein said hydrophobic A polymer block comprises 74% by weight of said block copolymer and said hydrophilic B polymer block comprises 26% by weight of said block copolymer.

6. The composition of claim 5 further comprising an excipient which will vary the lower critical solution temperature and increase the rate of gelation of said block copolymer.

7. The composition of claim 1, wherein said protein is selected from the group consisting of interferon consensus, interleukins, erythropoietins, granulocyte-colony stimulating factor (GCSF), stem cell factor (SCF), leptin (OB protein), interferons (alpha, beta, gamma), tumor necrosis factor (TNF), tumor necrosis factor-binding protein (TNF-bp), interleukin-1 receptor antagonist (IL-1ra), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), granulocyte macrophage colony stimulating factor (GM-CSF), megakaryocyte derived growth factor (MGDF), keratinocyte growth factor (KGF), thrombopoietin, platelet-derived growth factor (PGDF), novel erythropoiesis stimulating protein (NESP), tissue plasminogen activator (TPA), urokinase, streptokinase and kallikrein.

* * * * *

UNITED STATES PATENT AND TRADEMARK OFFICE
CERTIFICATE OF CORRECTION

PATENT NO. : 6,451,346 B1
DATED : September 17, 2002
INVENTOR(S) : Shah et al.

It is certified that error appears in the above-identified patent and that said Letters Patent is hereby corrected as shown below:

Column 1,
Line 21, change "erythrbpoiesis" to -- erythropoiesis --.

Column 2,
Line 2, change "esptcially" to -- especially --.
Line 35, change "liquidat" to -- liquid at --.

Column 12,
Line 5, change "(40 ml)land" to -- (40 ml) and --.
Line 8, change "in400" to -- in 400 --.
Line 62, change "980from" to -- 980 from --.

Column 15,
Line 41, change "f" to -- of --

Column 16,
Line 1, change "Viva" to -- Vivo --.

Signed and Sealed this

Fourth Day of March, 2003

JAMES E. ROGAN
*Director of the United States Patent and Trademark Office*